United States Patent
Roberts et al.

(10) Patent No.: US 7,365,188 B2
(45) Date of Patent: Apr. 29, 2008

(54) PROCESS FOR PRODUCING $N^4$-ACYL-5'-DEOXY-5-FLUOROCYTIDINE

(75) Inventors: Christopher R. Roberts, Berthoud, CO (US); Jim-wah Wong, Boulder, CO (US)

(73) Assignee: Roche Colorado Corporation, Boulder, CO (US)

(*) Notice: Subject to any disclaimer, the term of this patent is extended or adjusted under 35 U.S.C. 154(b) by 325 days.

(21) Appl. No.: 11/021,703

(22) Filed: Dec. 22, 2004

(65) Prior Publication Data
US 2005/0137392 A1 Jun. 23, 2005

Related U.S. Application Data

(60) Provisional application No. 60/532,266, filed on Dec. 22, 2003.

(51) Int. Cl.
C07H 19/06 (2006.01)
(52) U.S. Cl. ............... 536/27.11; 536/55.3; 536/28.51; 536/28.52
(58) Field of Classification Search ............ 536/27.11, 536/55.3, 28.51, 28.52
See application file for complete search history.

(56) References Cited

U.S. PATENT DOCUMENTS

| 4,966,891 A * | 10/1990 | Fujiu et al. ............... 514/49 |
| 5,453,497 A * | 9/1995 | Kamiya et al. ........... 536/28.52 |
| 5,472,949 A * | 12/1995 | Arasaki et al. ............ 514/49 |
| 5,476,932 A * | 12/1995 | Brinkman et al. ......... 536/55.3 |
| 2004/0166058 A1* | 8/2004 | Yang et al. ............... 424/1.49 |

FOREIGN PATENT DOCUMENTS

| EP | 0316704 B1 | 12/1995 |
| JP | 60-038395 | 2/1985 |
| JP | 60-038396 | 2/1985 |
| JP | 01-153696 | 6/1989 |
| WO | 2005/063786 A2 | 7/2005 |

OTHER PUBLICATIONS

[R] Nishimura et al.(I), "Studies on Synthetic Nucleosides. I. Trimethylsilyl Derivatives of Pyrimidines and Purines," Chemical and Pharmaceutical Bulletin, 12(3), 352-356 (1964).*
(S) Nishimura et al.(II), "Studies on Synthetic Nucleosides. II. Novel Synthesis of Pyrimidine Glucosides," Chemical and Pharmaceutical Bulletin, 12(3), 357-361 (1964).*
(T) Ninomiya et al., "Comparative Antitumor Activity and Intestinal Toxicity of 5'-Deoxy-5-fluorouridine and Its Prodrug Trimethoxybenzoyl-5'-deoxy-5-fluorocytidine," Japanese Journal of Cancer Research, 81(2), 188-195 (Feb. 1990).*
R] Nishimura et al.(I), "Studies on Synthetic Nucleosides. I. Trimethylsilyl Derivatives of Pyrimidines and Purines," Chemical and Pharmaceutical Bulletin, 12(3), 352-356 (1964).*
(T) Ninomiya et al., "Comparative Antitumor Activity and Intestinal Toxicity of 5'-Deoxy-5-fluorouridine and Its Prodrug Trimethoxybenzoyl-5'-deoxy-5-fluorocytidine,"Japanese Journal of Cancer Research, 81(2), 188-195 (Feb. 1990).*
PCT International Search Report, mailed Jun. 3, 2005 for PCT/EP2004/014281 (4 pages).
Nobuo Shimma et al., "The Design and Synthesis of a New Tumor-Selective Fluoropyrimidine Carbamate, Capecitabine", Bioorganic & Medicinal Chemistry 8 (2000) 1697-1706 (10 pages).

* cited by examiner

*Primary Examiner*—L. E. Crane
(74) *Attorney, Agent, or Firm*—Faegre & Benson, LLP

(57) ABSTRACT

The present invention provides a process for producing a $N^4$-acyl-5'-deoxy-5-fluorocytidine compound of the formula:

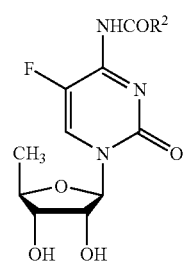

where $R^2$ is alkyl, cycloalkyl, aralkyl, aryl, or alkoxy.

25 Claims, No Drawings

PROCESS FOR PRODUCING N⁴-ACYL-5'-DEOXY-5-FLUOROCYTIDINE

CROSS-REFERENCE TO RELATED APPLICATION

This application claims the priority benefit of U.S. Provisional Patent Application No. 60/532,266, filed Dec. 22, 2003, titled "Process for Producing $N^4$-Acyl-5'-Deoxy-5-Fluorocytidine," which is incorporated herein by reference in its entirety. This application was also published as Publication No. U.S. 2005-0137392 on Jun. 23, 2005.

FIELD OF THE INVENTION

The present invention relates to a process for producing $N^4$-Acyl-5'-deoxy-5-fluorocytidine compounds.

BACKGROUND OF THE INVENTION $N^4$-Acyl-5'-deoxy-5-fluorocytidine compounds have antitumor activity. See, for example, *Japanese J. of Cancer Research*, 1990, 81, 188-195, which is incorporated herein by reference in its entirety. One method of producing such a compound from 5'-deoxy-5-fluorocytidine is described in Japanese Patent Application Kokai No. 153,696/1989, which is incorporated herein by reference in its entirety. However, due to the length of the process, this process is not amenable for a large-scale commercial process.

One conventional commercial process for producing $N^4$-acyl-5'-deoxy-5-fluorocytidine compounds involves synthesis of 5'-deoxy-5-fluoro-$N^4$,2',3'-triacylcytidine as an intermediate. See, for example, U.S. Pat. No. 5,453,497, issued Sep. 26, 1995, which is incorporated herein by reference in its entirety. This process requires a selective deacylation of hydroxy groups in the 2'- and 3'-positions to produce the final compounds. This method, along with an alternative process (see, for example, U.S. Pat. No. 5,476,932, issued Dec. 19, 1995, which is incorporated herein by reference in its entirety), is currently used to produce the anti-tumor agent in a commercial scale. However, these processes require the use of a large amount of carcinogenic halogenated solvent (e.g., methylene chloride), and tin (IV) chloride as a coupling catalyst.

Tin waste is not environmentally friendly and requires a special disposal procedure, thereby increasing the overall cost to the drug manufacture. Moreover, conventional commercial manufacturing processes for producing $N^4$-acyl-5'-deoxy-5-fluorocytidine compounds require isolation of intermediate products, thereby further increasing the overall manufacturing time and cost.

Japanese Patent Nos. 60038395 and 60038396, which are incorporated herein by reference in their entirely, discuss an effort to improve the process for production of $N^4$-acyl-5'-deoxy-5-fluorocytidine, via fluorination of cytidine and 5'-deoxycytidine in acetic acid/HF or trifluoroacetic acid solution. However, this method requires a large amount of Raney Ni (another heavy metal) for desulfurization to be environmentally feasible, and resulted in low yields of 5'-deoxycytidine.

*Chem. Pharm. Bull.* (Tokyo) 352 (1964), which is incorporated herein by reference in its entirety, discusses a method of acylating 5-fluorocytosine prior to the coupling step in an effort to provide a more efficient coupling process by using a less basic coupling partner for β-acetylfuranoside. Unfortunately, switching the sequence of coupling and acylation steps gave a higher amount of α-anomer formation, which is shown to be less stable than the β-anomer under the reaction conditions.

Besides the use of heavy metals in some conventional processes, there are other disadvantages in conventional commercial processes for producing $N^4$-acyl-5'-deoxy-5-fluorocytidine compounds. For example, some conventional processes use a relatively large quantity of methylene chloride as a solvent in many of the reactions. Halogenated solvents, such as methylene chloride, require special disposal treatment, thus attributing to the increase in the overall drug production cost. Moreover, halogenated solvents pose a greater health risk to workers than most non-halogenated solvents.

Another disadvantage of conventional processes is that the overall yield of $N^4$-acyl-5'-deoxy-5-fluorocytidine compounds is only about 62%. Any significant improvement in the overall yield will likely reduce the overall cost greatly for producing $N^4$-acyl-5'-deoxy-5-fluorocytidine compounds.

Therefore, there is a need for a process for producing $N^4$-acyl-5'-deoxy-5-fluorocytidine compounds that does not require the use of a heavy metal based catalyst. There is also a need for a process for producing $N^4$-acyl-5'-deoxy-5-fluorocytidine compounds that uses a significantly less amount of halogenated solvents, such as methylene chloride. There is also a need to improve the overall production yield of $N^4$-acyl-5'-deoxy-5-fluorocytidine compounds.

SUMMARY OF THE INVENTION

One aspect of the present invention provides a process for producing a $N^4$-acyl-5'-deoxy-5-fluorocytidine compound of the formula:

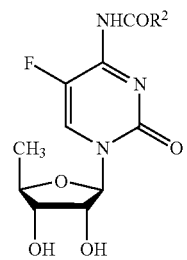

where $R^2$ is alkyl, cycloalkyl, aralkyl, aryl, or alkoxy.

In one particular embodiment, the process comprises:

(a) admixing 5-fluorocytosine of the formula:

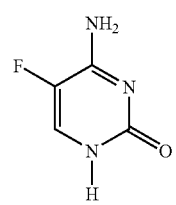

with a first silylating agent in the presence of an acid catalyst under conditions sufficient to produce a first silylated compound;

(b) admixing the first silylated compound with a β-2,3-diprotected-5-deoxy furanoside of the formula:

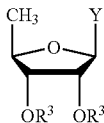

under conditions sufficient to produce a coupled product;

(c) admixing the coupled product with a second silylating agent to produce a second silylated product;

(d) acylating the second silylated product with an acylating agent of the formula:

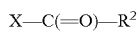

to produce an acylated product; and (e) selectively removing a covalently linked silyl moiety and the hydroxy protecting groups, $R^3$, under conditions sufficient to produce the $N^4$-acyl-5'-deoxy-5-fluorocytidine Compound of Formula I, where X is an acyl activating group;

Y is a leaving group;

$R^2$ is alkyl, cycloalkyl, aralkyl, aryl, or alkoxy; and $R^3$ is a hydroxy protecting group.

The 5-fluorocytosin compound of Formula II has more than one reactive site for silylation. Accordingly, the first silylated compound may comprise a mixture of different regioselectively silylated compounds. Similarly, the second silylated product also comprises more than one possible silylation reactive site, and thus may comprise a mixture of different regioselectively silylated products.

Preferably, processes of the present invention avoid using a heavy metal based catalyst, e.g., tin (IV) chloride, to produce the coupled product in step (b) above.

In another embodiment of the present invention, acetonitrile instead of a halogenated solvent, such as methylene chloride, which is often used in conventional commercial processes, is used as the reaction solvent in many of the steps described above, thereby making the process more environmentally friendly. Preferably, the reaction solvents used in the processes of the present invention do not comprise a halogenated solvent, such as methylene chloride.

Another advantage of processes of the present invention is a significant increase in the overall yield of the $N^4$-acyl-5'-deoxy-5-fluorocytidine compounds relative to conventional processes. This increase in the overall yield translates into further reduction in the overall production cost.

In yet another embodiment of the present invention, the intermediates of the reactions are not isolated and/or purified. It should be appreciated that one can perform isolation and/or purification step of one or more intermediates, if desired. However, by eliminating the need for isolating and/or purifying intermediate products, the overall cost and manufacturing time are further reduced significantly.

Another aspect of the present invention provides a compound of the formula:

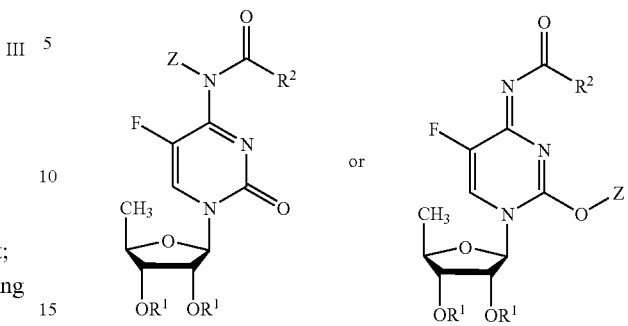

where $R^1$ is a hydroxy protecting group; Z is a tri(hydrocarbyl)silyl group; and $R^2$ is alkyl, cycloalkyl, aralkyl, aryl, or alkoxy.

DETAILED DESCRIPTION OF THE INVENTION

Definitions

Unless otherwise stated, the following terms used in the specification and claims have the meanings given below:

"Acyl" refers to a moiety of the formula —C(=O)—$R^z$, where $R^z$ is hydrocarbyl as defined herein.

"Acyl activating group" refers to a moiety which makes esterification of an acyl group significantly more reactive than a corresponding ester functional group. Exemplary acyl activating groups include anhydrides (i.e. a moiety of the formula R—C(=O)—O—), halides, thioesters, etc. A carbonyl compound containing an acyl activating group can be readily prepared from the corresponding carboxylic acid or esters by using a method known to one of ordinary skill in the art, including the use of anhydrides, or acyl halogenating agents. Exemplary acyl halogenating agents and general procedures for using the same are disclosed, for example, in *Comprehensive Organic Synthesis*, vol. 6, Trost, Fleming and Winderfeldt eds., Pergamon Press, 1991, pp. 301-319, and *The Chemistry of Acyl Halides*, Patai, ed., Interscience Publishers, 1972, pp. 35-64, all of which are incorporated herein by reference in their entirety.

"Alkyl" means a linear saturated monovalent hydrocarbon moiety of one to twenty two, preferably one to ten, and more preferably one to eight, carbon atoms or a branched saturated monovalent hydrocarbon moiety of three to twenty-two, preferably three to twelve, carbon atoms. Alkyl groups can optionally be substituted with one or more halides. Exemplary alkyl groups include methyl, ethyl, propyl, 2-propyl, n-butyl, iso-butyl, tert-butyl, pentyl, and the like.

"Alkylene" means a linear saturated divalent hydrocarbon moiety of one to twenty two, preferably one to ten, and more preferably one to eight, carbon atoms or a branched saturated divalent hydrocarbon moiety of three to twenty-two, preferably three to twelve, carbon atoms. Alkylene groups can optionally be substituted with one or more halides. Exemplary alkylene groups include methylene, ethylene, 2,2-dimethylethylene, propylene, 2-methylpropylene, butylene, pentylene, and the like.

"Alkoxy" refers to a moiety of the formula —$OR^a$, where $R^a$ is alkyl as defined herein.

"Aryl" means a monovalent monocyclic, bicyclic, or tricyclic aromatic hydrocarbon moiety. Aryl groups can optionally be substituted with one or more, preferably one, two or three, substituents. Preferred aryl substituents include alkyl, optionally protected hydroxy (including groups known as alkoxy and acyl), halo, nitro, and cyano. Exemplary aryl groups include optionally substituted phenyl, optionally substituted naphthyl, and optionally substituted anthracyl. Preferred aryl group is optionally substituted phenyl.

"Aralkyl" refers to a moiety of the formula $R^b$—$R^c$—, where $R^b$ is aryl and $R^c$ is alkylene as defined herein.

"Cycloalkyl" refers to a non-aromatic, preferably saturated, monovalent cyclic hydrocarbon moiety preferably of three to twenty-two, more preferably, three to twelve ring carbon atoms. Cycloalkyl can optionally be substituted with one or more, preferably one, two or three, substituents. Preferred cycloalkyl substituents are those described herein in reference to preferred substituents of an aryl group. Exemplary cycloalkyl groups include cyclopropyl, cyclobutyl, cyclopentyl, and cyclohexyl, each of which can be optionally substituted.

"Cycloalkylalkyl" refers to a moiety of the formula $R^d$—$R^e$—, where $R^d$ is cycloalkyl and $R^e$ is alkylene as defined herein.

The terms "halo" and "halide" are used interchangeably herein and refer to fluoro, chloro, bromo, or iodo. Preferred halides are fluoro and chloro with fluoro being a particularly preferred halide.

"Hydrocarbyl" refers a hydrocarbon moiety and includes alkyl, aryl, aralkyl, cycloalkyl, and cycloalkylalkyl which are specifically defined herein.

"Leaving group" has the meaning conventionally associated with it in synthetic organic chemistry, i.e., an atom or a group capable of being displaced by a nucleophile. Suitable leaving groups for a particular reaction are well known to one skilled in the art and include halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), and the like.

"Protecting group" refers to a grouping of atoms that when attached, e.g., covalently bonded, to a functional group reduces or prevents the reactivity of the functional group. Suitable protecting groups for a particular functional group for a given reaction are well known to one skilled in the art. See, for example, *Protective Groups in Organic Synthesis*, 3$^{rd}$ edition, T. W. Greene and P. G. M. Wuts, John Wiley & Sons, New York, 1999, and *Compendium of Synthetic Organic Methods*, Harrison and Harrison et al., Vols. 1-8, John Wiley and Sons, 1971-1996, all of which are incorporated herein by reference in their entirety. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilylethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated. Exemplary hydroxy protecting groups include benzyl and trityl ethers as well as alkyl ethers, tetrahydropyranyl ethers, trialkylsilyl ethers, allyl ethers, and others known to those skilled in the art.

"Tri(hydrocarbyl)silyl" refers to a moiety of the formula —Si$R^f_3$, where each $R^f$ is independently a hydrocarbyl. Preferably, each $R^f$ is independently selected from alkyl or aryl, or two $R^f$ groups together form a divalent cycloalkylene moiety (e.g., hexylene and butylene, commonly referred to as silacycloheptane or silacyclopentane derivatives).

The terms "treating", "contacting", "admixing", and "reacting" when referring to a chemical reaction, are used interchangeably herein and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there can be one or more intermediates which are produced in the mixture which ultimately lead to the formation of the indicated and/or the desired product.

As used herein, the terms "those defined above" and "those defined herein" when referring to a variable incorporates by reference the broad definition of the variable as well as preferred, more preferred and most preferred definitions, if any.

General Overview

One aspect of the present invention provides a process for producing a N$^4$-acyl-5'-deoxy-5-fluorocytidine compound of the formula:

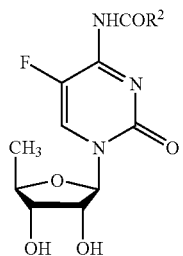

I where R$^2$ is alkyl, cycloalkyl, aralkyl, aryl, or alkoxy. Compounds of Formula I are pharmaceutically useful in treating a variety of diseases, including certain types of cancer. Therefore, there is a great commercial interest in an efficient and high yielding process for producing N$^4$-acyl-5'-deoxy-5-fluorocytidine compounds of Formula I.

The present invention provides processes for producing N$^4$-acyl-5'-deoxy-5-fluorocytidine compounds of Formula I that significantly increase yield and/or reduce the overall time and/or cost compared to conventional processes, for example, by eliminating isolation and/or purification of one or more, preferably all, intermediate products. In addition, processes of the present invention avoid the use of a heavy metal, which are often hazardous, and significantly reduce or eliminate the need for a halogenated reaction solvent, e.g., methylene chloride. Thus, processes of the present invention significantly reduce the overall production cost of the N$^4$-acyl-5'-deoxy-5-fluorocytidine compound of Formula I compared to conventional commercial processes and are environmentally more friendly.

Processes of the Present Invention

One aspect of the present invention for producing N$^4$-acyl-5'-deoxy-5-fluorocytidine compounds of Formula I comprises selectively removing a tri(hydrocarbyl)silyl group (i.e., silyl group), Z, and hydroxy protecting groups, R$^1$, from a compound of the formula:

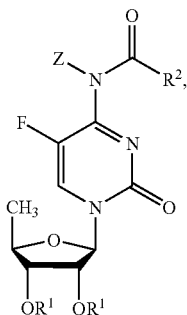

A-I

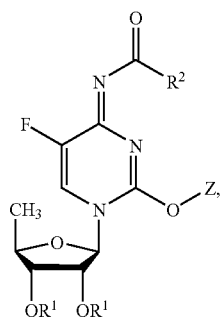

A-II

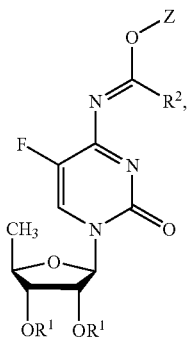

A-III

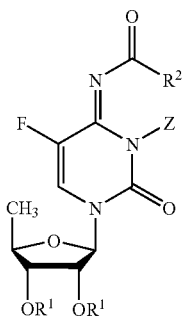

A-IV or a mixture thereof (herein collectively and/or individually referred to as "silyl-acyl fluorocytidine"), where $R^2$ is alkyl, cycloalkyl, aralkyl, aryl, or alkoxy. Preferably, $R^2$ is alkoxy, with pentoxy being a particularly preferred $R^2$ moiety.

Preferably, Z is a tri(alkyl)silyl group. A particularly preferred tri(alkyl)silyl groups include trimethylsilyl (TMS), t-butyldimethylsilyl (TBDMS), triisopropylsilyl (TIPS), and the like, with TMS being a particularly preferred Z moiety.

A preferred $R^1$ group is acyl. A particularly preferred $R^1$ is acetyl (i.e., a moiety of the formula —C(=O)—CH$_3$).

Preferably, removal of the silyl group is achieved by adding sodium bicarbonate and water. The silyl-acyl fluo-rocytidine of Formulas A-I to A-IV or a mixture thereof (collectively and/or individually referred to herein as Formula A) are generally produced by coupling an appropriate fluorocytosine moiety and the furanoside using a coupling catalyst, and then silylating and acylating the resulting coupled product. See infra. Quenching and washing processes of adding sodium bicarbonate and water typically remove at least a portion, preferably substantially all, of the catalyst and its residues as well as other impurities that may be present in the reaction mixture. Depending on the reaction conditions employed, the silyl group and the hydroxy protecting groups can be removed under the same reaction conditions, i.e., in a single-pot, or in a stepwise manner.

In general, when $R^1$ is acetyl moiety, the majority of the silyl group is removed by the addition of sodium bicaronate. However, only a relatively small amount, if any, of the hydroxy protecting groups is removed by sodium bicarbonate. Typically, a relatively stronger base than sodium bicarbonate is used to remove the hydroxy protecting group efficiently. Suitable bases for removing the hydroxy protecting groups include bases having pKa of conjugate acids ranging from about pH 12 to about pH 20, such as oxides, and hydroxides of alkaline metals, alkaline earth metals, transition metals, and rare earth metals. Typically, a hydroxide base, such as sodium hydroxide is used to remove an acyl hydroxy protecting group such as acetyl group.

While a variety of solvents are suitable in the hydrolysis step, a reaction solvent mixture comprising toluene and methanol is particularly useful. In particular, the biphasic system of toluene and aqueous basic solution (e.g., sodium hydroxide) in the presence of methanol, which is believed to be acting as a phase transfer reagent, is especially useful in methods of the present invention. One of the advantages of the two-phase reaction mixture is that it gives a clean and efficient hydrolysis. In addition, substantially all of the hydrolyzed substrate, which exists as the salt (e.g., sodium salt), partitions into the aqueous layer while most other organic impurities appear to remain in the toluene layer. In this manner, upon separation of the two solvent phases, a majority, if not most, of the impurities present from the earlier transformations (i.e., reactions) remain in the toluene layer and are separated from the desired product. Therefore, the selection of the solvents used in this step allows a simple purification of the desired product by simply separating the organic layer from the aqueous layer.

Typically, the reaction mixture for hydrolysis is cooled to about 0° C. and an aqueous solution of sodium hydroxide is added. The reaction mixture is then stirred for about 30 minutes, or until the hydrolysis is substantially complete. The aqueous layer is then separated to a pre-cooled, e.g., about 5° C. to 10° C., vessel. The separated organic layer is further extracted with water. The aqueous layers are then combined and acidified to a pH of about 3 to about 7, preferably about pH 4 to about pH 6, and more preferably about pH 5 to pH 5.5. The Compound of Formula I is then extracted with methylene chloride from the aqueous layer.

The Compound of Formula I can be purified using any of the purification processes known to one skilled in the art, such as chromatography, crystallization, and sublimation, etc. For a large scale production, crystallization is a preferred method of purifying the Compound of Formula I. Such a purification process is typically achieved using ethyl acetate and n-heptane mixture as the recrystallization solvent. Preferably, the ratio of ethyl acetate and n-heptane is about 50:50 to 60:40, with about 55:45 being the preferred ratio. During the crystallization process, the water content of the mixture is preferably kept at less than about 0.3%. A relatively high water content (e.g., about 0.3% or higher) results in a lower isolation yield and/or colored (e.g., yellowish) product. Therefore, it is preferred that the water content be less than about 0.5%, preferably about 0.3% or less, during the crystallization process.

The silyl-acyl fluorocytidine may be prepared by a variety of synthetic methods known to one skilled in the art. In one aspect of the present invention, the silyl-acyl fluorocytidine is produced by reacting a compound of the formula:

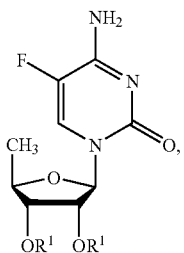

B-I

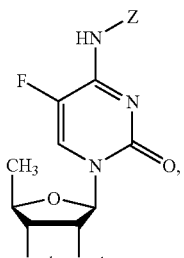

B-II

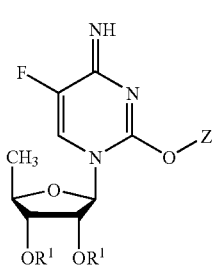

B-III or a mixture thereof; (each or combination of which are generically referred hereinafter as a compound of Formula B) with a silylating agent and followed by an acylating agent of the formula:

X—C(=O)—R² under conditions sufficient to produce the silyl-acyl fluorocytidine, where $R^1$, $R^2$, and Z are those defined herein and X is an acyl activating group. Preferably, the Compound of Formula B comprises a compound of formula B-II, B-III, or a mixture thereof. It should be appreciated that the sequence of silylation and acylation can be reversed depending on the reactivity of the silylating agent and the acylating agent; however, it is preferred to add the silylating agent prior to adding the acylating agent.

Preferably, X is an anhydride (i.e., a moiety of the formula R—C(=O)—O—, where R is hydrocarbyl) or halide. A particularly preferred acyl activating group is halide, with chloride being an especially preferred acyl activating group.

Processes of the acylation reaction typically comprise cooling the reaction mixture to a temperature in the range of about 0° C. to about 10° C. In one specific embodiment, n-pentyl chloroformate is used as the acylating agent and acetonitrile as the reaction solvent. Preferably, a mild base, such as pyridine, is also added to the reaction mixture as a promoter and/or acid scavenger.

While there are a variety of suitable silylating agents available that are well known to one skilled in the art, the preferred silylating agent to produce silyl-acyl fluorocytidine from the Compound of Formula B is hexamethyldisilazane. Typically, the amount of silylating agent added to the silyl-acyl fluorocytidine ranges from about 0.35 molar equivalents to about 0.45 molar equivalents relative to the amount of 5-fluorocytosine compound used.

A variety of solvents are suitable for preparing the silyl-acyl fluorocytidine from the Compound of Formula B, however, acetonitrile is a particularly useful solvent. By using acetonitrile as a reaction solvent, processes of the present invention avoid the use of a halogenated reaction solvent, e.g., methylene chloride.

Without being bound by any theory, it is believed that addition of the silylating agent to the Compound of Formula B "quenches" or deactivates reagent(s) and/or by-products (such as the coupling catalyst and/or acetic acid) that may be present in the mixture from a process that is used to produce the Compound of Formula B. See infra.

The Compound of Formula B may be prepared by a variety synthetic methods. In one particular aspect of the present invention, the Compound of Formula B is produced by silylating 5-fluorocytosine of the formula:

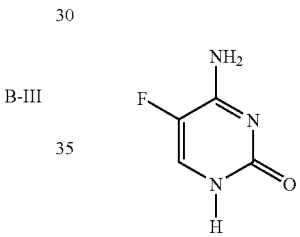

II with a first silylating agent in the presence of an acid catalyst under conditions sufficient to produce a first silylated compound. Suitable first silylating agents are well known to one skilled in the art. In one specific embodiment, the first silylating agent is hexamethyldisilazane.

In conventional processes, about 0.75 molar equivalents of the first silylating agent is used relative to the amount of 5-fluorocytosine. However, using such an amount results in poorer overall yield of the desired anomer (i.e., β-anomer) of the coupled product. See infra. Thus, the amount of first silylating agent used in silylating 5-fluorocytosine in processes of the present invention ranges from about 0.60 molar equivalents to about 0.70 molar equivalents of 5-fluorocytosine. A particularly preferred amount of the first silylating agent is about 0.65 molar equivalents of 5-fluorocytosine. In addition to finding an increase in undesired isomers when a relatively high amount (e.g., 0.75 molar equiv. or higher) of the first silylating agent is used in silylation, using a relatively small amount (e.g., 0.6 molar equiv. or less) of the first silylating agent results in an incomplete and/or slow coupling reaction in a subsequent coupling reaction with 5-fluorocytosine. See infra.

Often silylation of the Compound of Formula I comprises dissolving the reagents in a non-halogenated reaction solvent, preferably one that comprises acetonitrile. The reaction mixture is then heated under reflux in the presence of the first silylating agent and an acid catalyst. Suitable silylating catalysts are well known to one skilled in the art. However, a preferred silylating catalyst is triflic acid, which is preferably used in an amount ranging from about 0.01 to about 0.3 mol %, and more preferably in an amount of about 0.1 mol % relative to the amount of 5-fluorocytosine.

In one embodiment of the present invention, the first silylated compound is not purified but used directly in the next step. In some instances, the first silylated compound is subjected to a work-up process to quench and/or remove reagent(s) and/or reaction by-product(s) that may interfere with subsequent reactions. Typically, substantially all ammonia compound that may be formed during the first silylation process is removed, e.g., via evaporation or vacuum distillation. Without being bound by any theory, it is believed that removal of ammonia compound by-product of the first silylation reaction avoids formation of ammonium triflate in the subsequent coupling reaction. It is also believed that the first silylation reaction results in the formation of a mixture of silylated compounds of the formulas:

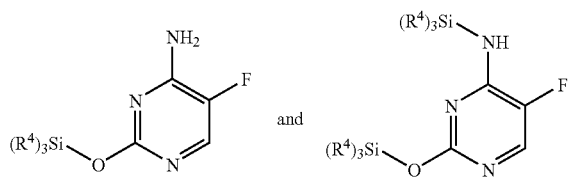

where each $R^4$ is independently hydrocarbyl.

In one particular embodiment of the present invention, the first silylated compound is coupled with a 2,3-diprotected-5-deoxy furanoside (preferably, the β-anomer) of the formula:

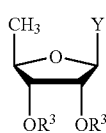

III without any work-up, isolation, and/or purification. It should be appreciated that while the β-anomer is preferred, the 2,3-diprotected-5-deoxy furanoside of Formula III can be α-anomer, β-anomer, or a mixture therefore. In the 2,3-diprotected-5-deoxy furanoside of Formula III above, Y is a leaving group; and $R^3$ is a hydroxy protecting group, preferably acetyl group (i.e., a moiety of the formula —C(=O)—CH₃). Preferably, this coupling process results in the formation of about 2% or less of α-anomer coupled product.

The coupling process typically comprises adding a coupling catalyst and the 2,3-diprotected-5-deoxy furanoside of Formula III to the first silylation reaction product. Suitable coupling catalysts include Lewis acids, such as trimethylsilyltriflate (TMSOTf), tin chloride, ferric chloride, cesium chloride, trimethylsilyl iodide (TMSI), trimethylsilyl bromide, trimethylsilyl nona-fluorobutanesulfonate, trimethylsilyl mesylate, trimethylsilyl trifluoroacetate, (TMSO)₂SO₂, TMSOSO₂Cl, dimethyl tin (IV) chloride, titanium tetrachloride and triflic acid. For a high yield and purity of the desired coupling product, the preferred coupling catalyst is triflic acid.

Generally, the amount of coupling catalyst used ranges from about 0.35 molar equivalents to about 0.65 molar equivalents of 5-fluorocytosine, with 0.60 molar equivalents being preferred. In the coupling reaction, the crude mixture of the first silylated product is cooled to a temperature range of from about 45° C. to about 55° C., preferably about 50° C., and the 2,3-diprotected-5-deoxy furanoside of Formula III is added to the reaction mixture along with additional acetonitrile.

To control the reaction temperature, the coupling catalyst (e.g., triflic acid) is added to the reaction mixture with cooling. Typically, after addition of the coupling catalyst the temperature of the reaction mixture is raised to about 50° C. and held for about 14-24 hours. The reaction mixture is then cooled to about 20° C. and carried on to the next step. Preferably, the crude reaction mixture is carried onto the next step without isolation or purification.

Unlike conventional processes, processes of the present invention eliminate the use of methylene chloride as a solvent and tin (IV) chloride catalyst in the coupling reaction. By avoiding the use of tin (IV) catalyst, processes of the present invention eliminate the tin catalyst filtration step which is often difficult and/or time consuming. While the overall amount of the silylating agent, e.g., hexamethyldisilazane, used is higher in processes of the present invention, the amount of hexamethyldisilazane used in the coupling process is actually lower in the processes of the present invention compared to conventional processes, e.g., 0.65 molar equivalents versus 0.75 molar equivalents of hexamethyldisilazane relative to the amount of 5-fluorocytosine used.

There are numerous advantages in processes of the present invention compared to conventional processes, such as higher yield, purity, and ease of product isolation. However, the processes of the present invention significantly reduce the amount of undesired α-anomer coupling product. In addition, compared to conventional processes, the processes of the present invention decrease the number of environmentally objectionable chemicals used, the length of time necessary for the reaction and result in a higher yield of Compound of Formula I. For example, processes of the present invention eliminate the use of tin (IV) chloride catalyst, eliminate a catalyst filtration step, reduce the amount of methylene chloride used, reduce or eliminate the need for isolating intermediates, and result in 68-85% overall yield of the Compound of Formula I, which is significantly higher than the 62% overall yield for conventional commercial processes.

Other additional objects, advantages, and novel features of this invention will become apparent to those skilled in the art upon examination of the following examples, which are intended to be illustrative rather than limiting.

EXAMPLES

This example illustrates a process for producing $N^4$-acyl-5'-deoxy-5-fluorocytidine from 5-fluorocytosine.

To a 4-L reaction vessel, equipped with a nitrogen inlet, mechanical stirrer, bottom valve (or funnel), reflux condenser and thermocoupler is added 200 g of 5-fluorocytosine, 162 g of hexamethyldisilazane, 400 g of acetonitrile and 138 μL of triflic acid. The reaction mixture is heated to reflux for 2 hours and then cooled to about 20° C. To this resulting mixture is added 431 g of β-acetylfuranoside, 400 g of acetonitrile, and 140 g of triflic acid, while maintaining a temperature of 55° C. or less. The reaction mixture is heated to 50° C.±5° C. for about 14 hours and then cooled to 20° C. About 100 g of hexamethyldisilazane is then added and the mixture is cooled to 5° C. after which 123 g of pyridine is added, and the batch is cooled again to 5° C. before 303 g of n-pentyl chloroformate is added while maintaining a temperature of less than 10° C. The resulting mixture is stirred for 30 minutes and then for 2 hours at about 20° C. The reaction mixture is then cooled to between 0 and 5° C., and about 260 g of sodium bicarbonate is added followed by about 600 g of water over the course of 30 to 60 minutes while maintaining a temperature of less than 10° C. The resulting mixture is stirred for 30 to 60 minutes and allowed to settle.

The organic layer containing the desired intermediate is separated, washed with a sufficient amount of water to remove substantially all of the triflate salts and concentrated. The resulting residue is diluted with about 1400 mL of toluene and cooled to about 5° C. before adding about 1000 mL of 1% hydrochloric acid. The mixture is stirred, then allowed to settle, and the aqueous layer is removed. This stirring and separation of aqueous layer process is repeated once with 1000 mL of saturated aqueous sodium bicarbonate, and twice with 1000 mL of water. About 200 mL to 600 mL of methanol is then added to the organic layer and the mixture is cooled to below 0° C. before adding about 310 g of aqueous sodium hydroxide solution (15%) while maintaining the temperature of less than 5° C. The resulting mixture is stirred for 30 minutes and then allowed to settle. The aqueous layer is separated and the organic layer is extracted with about 300 mL of water. The aqueous layers are combined and cooled to about 5° C.

The pH of aqueous layer is adjusted to about 4 to 5.9, typically to pH of about 5.25. The aqueous layer is then extracted with one or more portions of methylene chloride. The organic layers are combined, washed with water, filtered, and concentrated under vacuum while maintaining the temperature at about 35° C. or below.

The residue is diluted with about 3200 mL of ethyl acetate and again concentrated under vacuum. Karl Fisher analysis is performed when ~1600 mL of ethyl acetate is removed. If the water level is >0.3%, then 1600 mL of additional ethyl acetate is added and the process repeated until the water level of <0.3% is reached. If the water level is <0.3% then 1150 mL of n-heptane is added and concentrated to a volume of about 1600 mL. The solvent composition is analyzed and n-heptane is added, if needed, to bring the ethyl acetate:n-heptane ratio to 55:45 vol:vol. The product is crystallized by cooling and maintaining the temperature of the mixture at about 10° C. for at least one hour. The resulting solid is filtered, washed with about 400 mL of cold (0-5° C.) ethyl acetate and 400 mL n-heptane, and dried under vacuum. Yield: 68-85%

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All publications, patents, and patent applications cited herein are hereby incorporated by reference in their entirety for all purposes.

What is claimed is:

1. A process for producing a $N^4$-acyl-5'-deoxy-5-fluorocytidine compound of formula:

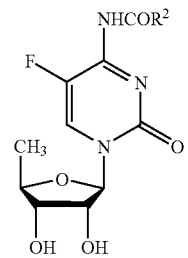

wherein $R^2$ is alkyl, cycloalkyl, aralkyl, aryl, or alkoxy, said process comprising:

(a) admixing 5-fluorocytosine of formula:

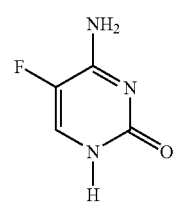

with a first silylating agent in the presence of an organic acid catalyst to produce a first silylated compound;

(b) admixing the first silylated compound with a 2,3-diprotected-5-deoxy furanoside of formula:

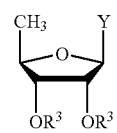

to produce a coupled product,
wherein
Y is a leaving group; and
$R^3$ is a hydroxy protecting group;

(c) admixing the coupled product with a second silylating agent to produce a second silylated compound, wherein the second silylating agent may be the same as or different from the first silylating agent;

(d) acylating the second silylated compound with an acylating agent of formula:

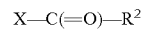

X—C(=O)—$R^2$ to produce an acylated product,
wherein
X is introduced as an acyl activating moiety by reaction with a reagent selected from the group consisting of: anhydrides, acyl halides, and thioesters; and
$R^2$ is alkyl, cycloalkyl, aralkyl, aryl, or alkoxy; and (e) adding at least one base to the acylated product to selectively remove a covalently linked silyl moiety and the hydroxy protecting groups, $R^3$, to produce the $N^4$-acyl-5'-deoxy-5-fluorocytidine compound of Formula I.

2. The process of claim 1, wherein the first silylating agent is hexamethyldisilazane.

3. The process of claim 2, wherein the amount of first silylating agent present in step (a) ranges from about 0.60 molar equivalents to about 0.70 molar equivalents relative to the amount of 5-fluorocytosine.

4. The process of claim 3, wherein the amount of first silylating agent present in step (a) is about 0.65 molar equivalents relative to the amount of 5-fluorocytosine.

5. The process of claim 1, wherein said coupling step (b) results in the formation of a coupled product in α-anomeric form of about 2% or less.

6. The process of claim 5, wherein the organic acid catalyst is triflic acid.

7. The process of claim 6, wherein the amount of organic acid catalyst present in coupling step (b) ranges from about 0.35 molar equivalents to about 0.65 molar equivalents relative to the amount of 5-fluorocytosine.

8. The process of claim 1, wherein the reaction temperature range of said step (b) of producing the coupled product is from about 45° C. to about 55° C.

9. The process of claim 8, wherein the reaction temperature of said step (b) of producing the coupled product is about 50° C.

10. The process of claim 1, wherein the second silylating agent of said step (c) is hexamethyldisilazane.

11. The process of claim 10, wherein the amount of second silylating agent present in step (c) ranges from about 0.35 molar equivalents to about 0.45 molar equivalents relative to the amount of 5-fluorocytosine.

12. The process of claim 1, wherein $R^3$ is acetyl.

13. The process of claim 1, wherein the base is an alkoxide or a hydroxide.

14. The process of claim 1, wherein the 2,3-diprotected-5-deoxy furanoside of Formula III is in the β-anomeric form.

15. A process for producing a $N^4$-acyl-5'-deoxy-5-fluorocytidine compound of formula:

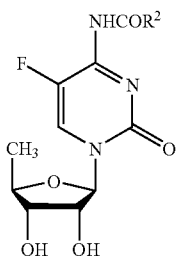

I comprising admixing at least one compound of formulas:

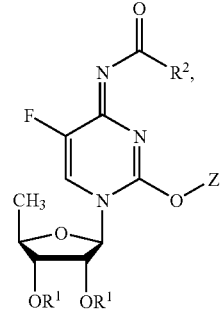

A

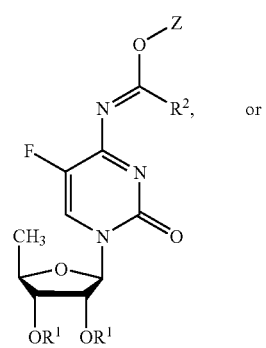

B

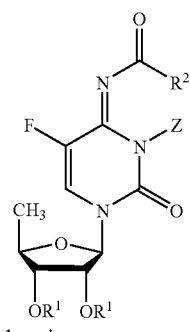

C or

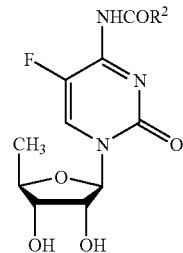

D wherein
$R^1$ is a hydroxy protecting group;
Z is a tri(hydrocarbyl)silyl group; and
$R^2$ is alkyl, cycloalkyl, aralkyl, aryl, or alkoxy;
with a base to selectively remove the trialkylsilyl group, Z, and the hydroxy protecting groups, $R^1$, to produce the $N^4$-acyl-5'-deoxy-5-fluorocytidine compound of Formula I.

16. A compound selected from the group consisting of the compounds defined in claim 15 at line 6 by the chemical formulas associated with the letters A, B, C and D.

17. The compound of claim 16, wherein Z is trimethylsilyl.

18. The compound of claim 17, wherein $R^2$ is alkoxy.

19. The compound of claim 18, wherein $R^2$ is pentoxy.

20. A process for producing a $N^4$-acyl-5'-deoxy-5-fluorocytidine compound of formula:

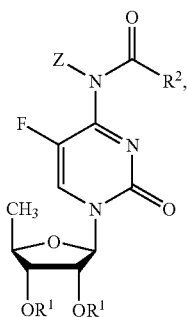

I comprising:
(a) successively admixing a reaction mixture comprising a 5-fluorocytidine compound of at least one of formulas:

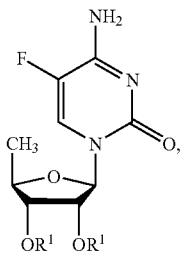 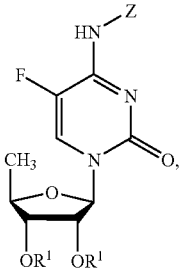

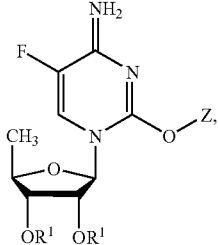

or a mixture thereof;
with a silylating agent and an acylating agent, the acylating agent of formula:

X—C(=O)—R² to produce a silylated and acylated compound of at least one of formulas:

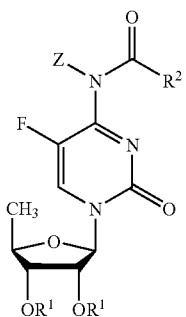 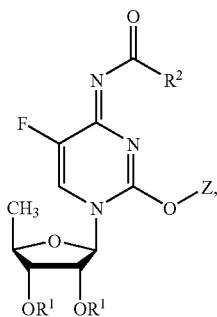

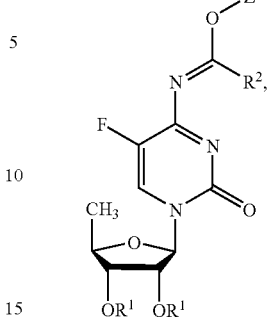 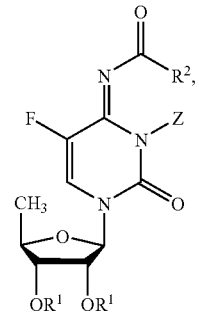

or a mixture thereof,
wherein
$R^1$ is a hydroxy protecting group;
$R^2$ is alkyl, cycloalkyl, aralkyl, aryl, or alkoxy;
X is introduced as an acyl activating group as defined in claim 1; and
Z is a tri(hydrocarbyl)silyl group; and
(b) adding at least one base to selectively remove the silyl group and the hydroxy protecting groups from the silylated and acylated compound to produce the $N^4$-acyl-5'-deoxy-5-fluorocytidine compound of Formula I.

21. The process of claim 20, wherein the silylating agent is hexamethyldisilazane.

22. The process of claim 21, wherein the amount of silylating agent present in step (a) ranges from about 0.35 molar equivalents to about 0.45 molar equivalents relative to the amount of the 5-fluorocytosine compound.

23. The process of claim 20, wherein $R^2$ is pentoxy.

24. The process of claim 20, wherein said process comprises acetonitrile as a reaction solvent.

25. The process of claim 20, wherein said step of removing the silyl group and the hydroxy protecting groups comprises toluene as a solvent.

* * * * *